United States Patent [19]

Biollaz et al.

[11] 4,052,421
[45] Oct. 4, 1977

[54] NEW 13-ETHINYL-STEROIDS AND PROCESSES FOR THEIR MANUFACTURE

[75] Inventors: Michel Biollaz, Basel; Jaroslav Kalvoda, Binningen, both of Switzerland

[73] Assignee: Ciba-Geigy Corporation, Ardsley, N.Y.

[21] Appl. No.: 650,653

[22] Filed: Jan. 20, 1976

[30] Foreign Application Priority Data

Jan. 30, 1975 Switzerland .......... 1123/75

[51] Int. Cl.² .............................. C07J 1/00
[52] U.S. Cl. .................. 260/397.5; 260/239.55 C; 260/397.3; 260/397.4
[58] Field of Search .......... 260/397.5, 239.55 C, 260/397.4; 424/243, 241

[56] References Cited

U.S. PATENT DOCUMENTS

| 3,267,005 | 8/1966 | Foell et al. .......... 195/51 |
| 3,798,215 | 3/1974 | Galantay et al. .......... 260/397.5 |
| 3,959,322 | 5/1976 | Hughes et al. .......... 260/397.5 |

Primary Examiner—Elbert L. Roberts
Attorney, Agent, or Firm—John J. Maitner

[57] ABSTRACT

A new class of 13-ethinyl-steroids is prepared by a novel process comprising Wittig reaction of a 13-formyl steroid with a chloro- or bromomethylenephosphorane and dehydrohalogenation of the intermediate 13-(2-halogenovinyl)steroid with an extremely strong base. Preferred products are those of the formula

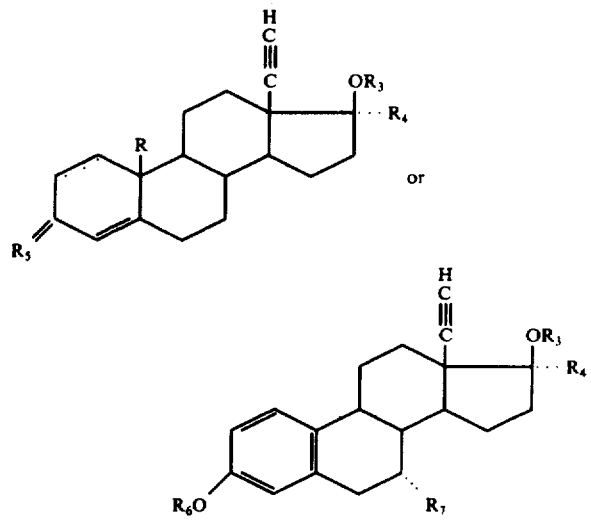

wherein R denotes a hydrogen atom or the methyl group, $R_3$ denotes a hydrogen atom or a lower alkyl or lower alkanoyl group, $R_4$ denotes a hydrogen atom or a lower aliphatic hydrocarbon radical, or $R_3$ and $R_4$ together denote a C—O linkage, $R_5$ denotes the oxo group, a hydrogen atom together with an esterified or free hydroxyl group, or two hydrogen atoms, $R_6$ denotes a hydrogen atom or a lower alkyl group, and $R_7$ denotes a hydrogen atom or the methyl group, it also being possible for an additional 1,2-double bond to be present in compounds in which R is the methyl group. These compounds are pharmacologically active in a manner analogous to that of natural sexual hormones, and are distinguished as blockers of the secretion of pituitary gonadotrophins; accordingly, they are useful in medicine for the corresponding indications and for fertility control.

14 Claims, No Drawings

13-ETHINYL-STEROIDS AND PROCESSES FOR THEIR MANUFACTURE

The present invention relates to a hitherto unknown group of compounds, that is to say the 13-ethinyl-steroids, as well as to processes for their manufacture. In particular, the invention relates to the compounds of the general formula I

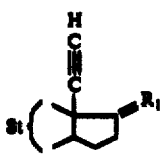

wherein St represents the remaining part of the steroid skeleton, which is optionally substituted and/or otherwise modified, and $R_1$ denotes an optionally ketalised oxo group or an α-oriented or, preferably, β-oriented, optionally etherified or esterified hydroxyl group together with a hydrogen atom or with an optionally halogenated lower aliphatic hydrocarbon radical, as well as processes for the manufacture of these compounds.

The compounds according to the invention belong, above all, to the derivatives of the D-series, which occurs in nature, but they can also be present as derivatives of the L-series, which is accessible by total synthesis, or as racemic mixtures of the two antipodes.

Wherever it occurs in connection with an organic radical, the term "lower" designates a corresponding radical with at most 7, but preferably 1 to 4, carbon atoms.

The radical St consists of the rings A and B (carbon atoms C-1 to C-10) and the remaining carbon atoms of the ring C (C-11 and C-12) and can also carry the angular methyl group (C-19) in the 10-position. It can also be modified in other ways, for example have a structure with enlarged or contracted rings, such as the A-nor or the A-nor-B-homo structure and/or display ring bridging, for example the 3α,5-cyclo-linkage. The rings A, B and C can take up various configurations relative to one another, such as, for example, the 5α,9β,10α or the 5β,9β,10α configuration, but above all the 5α,9α,10β or the 5β,9α,10β configuration. The radical St can have one, two or more double bonds, such as in the 1,2-, 2,3-, 3,4-, 5,10-, 6,7-, 9,10-, 9,11- or 11,12- positions but above all in the 4,5- or 5,6-positions, and in the absence of a substituent in the 10-position, three such double bonds can form an aromatic system, especially in the ring A. The radical St can also be substituted by free, etherified and, especially, esterified hydroxyl groups, for example in the 3- and/or 19-positions, above all in the 3β-position, by free or ketalised oxo groups, especially in the 3- and/or 11-position, by lower alkyl radicals, for example in the 7α- or, especially, 6α-position or by halogen atoms, such as bromine, or especially chlorine or fluorine atoms, especially in the 2- or 6-position.

A lower alkyl radical is, for example a n-propyl, i-propyl, n-butyl, i-butyl, sec.-butyl or tert.-butyl radical or a branched or, preferably, straight-chain pentyl, hexyl or heptyl radical, but above all an ethyl or methyl radical. A lower aliphatic hydrocarbon radical is to be regarded as a lower alkyl radical, for example one of those already mentioned, which optionally also has one or two multiple bonds, that is to say double bonds or acetylene bonds, such as, for example, a lower alkenyl, lower alkinyl and allenyl radical, for example, a vinyl, allyl, methallyl, propargyl, hexadiinyl and, above all, ethinyl radical.

The lower aliphatic hydrocarbon radical already discussed can be substituted by one or more identical or different halogen atoms, which are located, above all, in the α- and/or β-position (corresponding to the 20-position and the 21-position respectively of the steroid numbering). Possible halogen atoms are, in particular, chlorine and fluorine.

A ketalised oxo group is derived, in particular, from lower alkanols, for example from methanol or ethanol, or preferably from α- or β-lower alkanediols, for example 1,2- or 1,3-propanediol or, above all, ethylene glycol; however, it can also be derived from the corresponding sulphur analogues of the alcohols mentioned and can have sulphur atoms in place of one or both of the oxygen atoms.

An etherified hydroxyl group is derived, in particular, from a lower alkanol, preferably a straight-chain lower alkanol, for example methanol, ethanol, propanol and butanol, an aryl-lower alkanol, preferably a phenyl-lower alkanol, for example benzyl alcohol or triphenyl-methylcarbinol, or from an oxygen-containing heterocyclic alcohol, for example 2-tetrahydropyranol or 2-tetrahydrofuranol. However, it can also formally be derived from a 1-lower alkoxy-lower alkanol, for example 1-butoxyethanol; the 1-butoxyethoxy group is to be mentioned as an example of an etherified hydroxyl group of this type. An etherified hydroxyl group can also be located on a carbon atom which carries a double bond going to an adjacent carbon atom, so that an enol ether grouping is present. This grouping is then, at the same time, a protected oxo group; a particularly important example to be mentioned is the $\Delta^{3,5}$-3-enol ether grouping, which formally is derived from the enol form of the $\Delta^4$-3-oxo grouping.

An etherified hydroxyl group is, however, also a silyloxy group which is substituted on the silicon atom by three identical or different hydrocarbon radicals, especially lower alkyl radicals, such as those mentioned above, for example a tri-lower alkylsilyloxy group, above all the trimethylsilyloxy group or the dimethyl-tert.-butylsilyloxy group.

An esterified hydroxyl group is derived, in particular, from an inorganic oxygen-containing acid, for example one of the sulphuric or phosphoric acids, or preferably from an organic acid, for example a sulphonic acid, for example an aromatic sulphonic acid, such as benzenesulphonic acid, toluenesulphonic acid or p-bromobenzenesulphonic acid, or an alkanesulphonic acid such as methanesulphonic acid, or, in particular, from a carboxylic acid.

Possible carboxylic acid components in an esterified hydroxyl group are, above all, the carboxylic acids customary in steroid chemistry, for example monocarboxylic acids with at most 18 carbon atoms, such as aliphatic carboxylic acids, especially formic acid or a lower alkanecarboxylic acid, the lower alkyl radical of which is one of those mentioned above, especially propionic acid, butyric acid, isobutyric acid, valeric acid, is valeric acid, oenanthic acid and diethylacetic acid and, above all, caproic acid, trimethylacetic acid and acetic acid; but also corresponding halogenated lower alkanecarboxylic acids, such as chloroacetic acid, trichloroacetic acid or trifluoroacetic acid; as well as caprylic acid, pelargonic acid, capric acid, lauric acid, myristic acid, palmitic acid and stearic acid, undecylic acid and undecylenic acid, elaidic acid and oleic acid; cycloaliphatic or cycloaliphatic-aliphatic monocarboxylic acids, for example cyclopropane-, cyclobutane-, cyclopentane- and cyclohexane-carboxylic acid and, respectively, cyclopropyl- or cyclobutyl-methanecarboxylic acid and a cyclopentyl- or cyclohexyl-ethanecarboxylic acid; aromatic carboxylic acids, for example benzoic acids which are optionally substituted by fluorine, chlorine, bromine, hydroxyl, lower alkoxy, lower alkyl or nitro groups; aryl- or aryloxy-lower alkanecarboxylic acids and their analogues which are unsaturated in the chain, for example phenylacetic acids or, respectively, phenoxyacetic acids, phenylpropionic acids and cinnamic acids which are optionally substituted as indicated above for benzoic acid; and heterocyclic acids, for example furane-2-carboxylic acid, 5-tert.-butylfurane-2-carboxylic acid, 5-bromofurane-2-carboxylic acid, thiophene-2-carboxylic acid, nicotinic acid or isonicotinic acid, 3-(4-pyridyl)-propionic acid, and pyrrole-2- or -3-carboxylic acids which are optionally substituted by lower alkyl radicals, but also corresponding dicarboxylic acids with at most 12 carbon atoms, for example succinic acid, glutaric acid, adipic acid and phthalic acid, as well as corresponding α-amino acids, especially α-amino-lower alkanecarboxylic acids, preferably those in the configuration which occurs in nature, for example glycine, proline, leucine, valine, tyrosine, histidine and asparagine, as well as glutamic acid and aspartic acid. The new 13-ethinyl-steroids according to the invention can be used as intermediate products for the synthesis of valuable active compounds for human medicine and veterinary medicine, especially for hormone therapy and for controlling fertility. Several of these compounds, for example the compounds singled out in particular further below, at the same time themselves exhibit a biological activity and can, accordingly, be used direct as active compounds in the above-mentioned field of application.

The 13-ethinyl-steroids according to the invention are obtainable according to a novel chemical process which is characterized in that a corresponding 13-formyl compound of the general formula

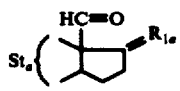

(II)

wherein $St_a$ denotes a radical which corresponds to the radical St characterized above and in which, apart from the 11-oxo group, there are no free oxo groups, and $R_{1a}$ denotes a radical which corresponds to the radical $R_1$ characterised above and in which the oxo group is present in a ketalised form, is subjected to a Wittig reaction with a halogenomethylenephosphorane compound and a resulting 13-(2-halogenovinyl) compound is dehydrohalogenated and, if desired, following the first and/or the second reaction stage, the radicals St and $R_1$, or, respectively, $St_a$ and $R_{1a}$, are modified, within the scope of their definition, in a manner which is in itself known by, for example, above all liberating protected oxo groups and/or esterified or etherified hydroxyl groups, but also by carrying out further conversions customary in steroid chemistry, especially by esterifying or etherifying hydroxyl groups or by oxidising them to oxo groups, ketalising oxo groups, or converting them into enol ethers or enol esters, or reducing them to hydroxyl groups, optionally introducing a hydrocarbon radical at the same time, and/or introducing further double bonds, optionally with aromatisation. These subsequent conversions can each be carried out on their own or they can be carried out in appropriate combinations.

In the starting materials of the formula II, any oxo groups which may be present are, as already indicated, in a ketalised form or in a protected form as enol ethers or enol esters; exceptions are the 13-formyl group which is to be converted and which accordingly must remain free, and also the 11-oxo group, the reactivity of which is reduced by its steric position to such an extent that, under the reaction conditions employed, it remains unaffected even without protection.

The other general and preferred structural characteristics and substituents are identical to those of the end products of the formula I and, in the 17-position, a substituent with very steric requirements, such as an ethylenedioxy group or a lower alkanoyloxy group, is particularly advantageous. It is advantageous for the course of the dehydrohalogenation if any hydroxyl groups which may be present in the intermediate 13-(2-chlorovinyl) compounds, and, above all, the 17β-hydroxyl group, are protected by etherification. Particularly, suitable for this purpose are silyl ethers for example tri-lower alkylsilyl ethers, especially trimethylsilyl ether or dimethyl-tert.-butylsilyl ether.

The halogenomethylenephosphorane compounds used for the Wittig reaction are chloro- or bromo-methylenephosphorane compounds which carry 3 hydrocarbon radicals on the phosphorus atom. These hydrocarbon radicals can be identical or different, acyclic or carbocyclic; in particular, they are lower alkyl radicals, for example those mentioned above, or aryl radicals, above all phenyl radicals. Particularly preferred reagents which may be mentioned are bromomethylenetriphenylphosphorane and chloromethylenetriphenylphosphorane, which are prepared, directly prior to the reaction, in the reaction mixture from bromomethyl-triphenyl-phosphonium bromide or, respectively, chloromethyl-triphenyl-phosphonium chloride, with butyl-lithium. The reaction takes place in a manner which is in itself known and which is customary for the Wittig reaction. Open-chain or cyclic ethers, such as diethyl ether, diisopropyl ether, ethylene glycol dimethyl ether or ethylene gylcol diethyl ether, tetrahydropyrane and, in particular, tetrahydrofurane, or also aliphatic or carbocyclic hydrocarbons, for example saturated carbocyclic hydrocarbons, such as cyclopentane or cyclohexane, aromatic carbocyclic hydrocarbons, such as benzene, toluene or xylenes, and especially aliphatic saturated hydrocarbons, preferably those which are liquid under atmospheric pressure and at room temperature, such as pentanes, hexanes, heptanes and octanes, are used as preferred solvents. It is also possible to combine several of the solvents mentioned with one another. Preferably, the reaction is carried out with the exclusion of moisture and in an inert atmosphere, such as under nitrogen or, especially, argon. Despite the steric hindrance at C-18 and the bulky reagent, the reaction surprisingly proceeds under relatively mild conditions, usually at room temperature. If necessary or advantageous, the reaction can also be carried out at temperatures of −20° up to the boiling point of the reaction mixture. Usually, a mixture of the corresponding cis- and trans-isomers of the 13-(2- halogenovinyl) compounds is obtained from the reaction and this can be separated into its individual components by physical methods, especially chromatography. The two isomers and the mixture thereof are all virtually equally suitable for further processing by dehydrohalogenation.

The dehydrohalogenation is carried out by means of extremely strong bases in a manner which is in itself known. For example, potassium tert.-butylate in a polar solvent, such as tert.-butanol or dimethylsulphoxide, or an alkali metal amide, such as lithium amide, sodium amide or potassium amide, preferably in liquid ammonia, is used as an extremely strong base. Preferred extremely strong bases are, however, organometallic compounds, especially those derived from the alkali metals, such as potassium, sodium and, above all, lithium. Possible hydrocarbon radicals for these organometallic compounds are aromatic carbocyclic radicals, such as phenyl radicals, but preferably lower alkyl radicals, for example those mentioned and, amongst these, above all the butyl radical. Butyl-lithium is used as a particularly preferred dehydrohalogenating reagent. The dehydrohalogenation by means of organometallic compounds is appropriately carried out in the presence of inert solvents which, under the reaction conditions employed, react neither with the reactants nor with the products. Solvents of this type which are used are preferably carbocyclic hydrocarbons, for example saturated carbocyclic hydrocarbons, such as cyclopentane, cyclohexane, cycloheptane or decahydronaphthalene, or aromatic carbocyclic hydrocarbons, such as benzene, toluene or xylenes, and, in particular, aliphatic saturated hydrocarbons, preferably those which are liquid under atmospheric pressure and at room temperature, such as pentanes, hexanes, heptanes or octanes, as well as mixtures of these solvents. The reaction temperature depends on the specific properties of each reaction mixture and in general is between 0° and 100°, preferably between 30° and 70°.

Subsequent liberation of the protected oxygen-containing functional groups in the resulting process products is carried out in a manner which is in itself known, preferably by hydrolysis. Ketalised oxo groups and etherified hydroxyl groups (including silyl ethers) are preferably hydrolysed under the conditions of acid catalysis in the presence of an inorganic acid, for example sulphuric acid or a hydrogen halide acid, such as hydrochloric acid, hydrobromic acid or hydriodic acid, or of an organic acid, for example a sulphonic acid, such as p-toluenesulphonic acid or sulphosalicyclic acid, or of a relatively strong carboxylic acid, such as oxalic acid or formic acid. Analogously, enol ethers are also hydrolysed to the corresponding oxo derivatives. Esterified hydroxyl groups and enol-acylated oxo groups can be hydrolysed under acic conditions; however, they are preferably hydrolysed using base catalysis. Hydroxides, carbonates or bicarbonates of the alkali metals, especially of sodium or potassium, are preferably used as basic catalysts. Esterified hydroxyl groups can also be liberated by reduction, for example by the action of an ester-reducing agent, such as a complex hydride or diborane.

Subsequent esterification or etherification of hydroxyl groups in the resulting compounds is also carried out in a manner which is in itself known. For esterification, for example, the compound to be esterified is treated with excess acid, for example with formic acid, or with a reactive derivative, of an acid, for example with a derivative of one of the acids indicated above, especially with an anhydride or an acid halide, advantageously in the presence of a tertiary base, such as pyridine, quinoline or N-ethyl-piperidine.

For etherification, for example, the compounds to be etherified are treated with reactive derivatives of alcohols, for example with their esters with strong acids, such as halides, sulphates or sulphonic acid esters, possible alcohol components being, in particular, one of the abovementioned alcohols. Preferably, the reaction is carried out in the presence of basic agents. In order to form tetrahydropyranyl ethers and analogous ethers, a corresponding unsaturated derivative, such as 2,3-dihydropyrane or a vinyl lower alkyl ether, for example vinyl butyl ether, is preferably used as the reagent and the reaction is carried out under conditions of acid catalysis, preferably in the presence of organic sulphonic acid.

The silyl ethers, for example the hydroxy compounds etherified with tri-lower alkylsilyl groups, such as trimethylsilyl groups or dimethyl-tert.-butylsilyl groups, can be prepared by treating the corresponding hydroxy compounds with an appropriate silylating agent, such as trimethylchlorosilane, dimethyl-tert.-butyl-chlorosilane, hexamethyl-disilazane, trimethylsilylamine, trimethylsilyldiethylamine, dimethyl-tert.-butylsilylimidazole, N-trimethylsilylacetamide or bis-(trimethylsilyl)-acetamide, in an anhydrous solvent, such as dimethylformamide, dimethylsulphoxide or acetonitrile, optionally in the presence of an anhydrous base, such as triethylamine, piperidine, pyridine or imidazole.

The ketalisation, enol-acylation and the formation of enol ethers, which are to be carried out if appropriate, in particular in order to protect the oxo groups, are also effected in a manner which is in itself known, in particular under the conditions of acid catalysis and, if appropriate, using dehydrating agents or azeotropic distillation. For ketalisation, for example, lower alkanols, such as methanol or ethanol, and especially α- and β-glycols, such as 1,2- or 1,3-propanediol and 1,2- or 2,3-butanediol and, above all, ethylene glycol, or reactive derivatives of these alcohols, such as acetals or ketals, especially those in which the carbonyl component is readily volatile, such as, for example, 2,2-dimethyl-1,3-dioxolane, are used. Analogous thioketals are obtained in an analogous manner, but starting from the sulphur analogues of the abovementioned alcohols, above all from 1,2-ethanedithiol or its reactive derivatives.

The reagent used to form the enol ethers is preferably an ortho-ester of a lower alkanol, especially of methanol or ethanol, with a lower aliphatic carboxylic acid, especially formic acid; particularly preferred reagents are methyl orthoformate and, above all, ethyl orthoformate. Enol-acylation is advantageously carried out by reaction with a reactive derivative of the desired carboxylic acid under acid catalysis; preferably, an anhydride, such as acetic anhydride, is used as the reagent and an organic acid, such as benzene-sulphonic acid, p-toluenesulphonic acid, salicylsulphonic acid or camphor-sulphonic acid, is used as the catalyst. Ketenes, especially unsubstituted ketene, can also be used as reactive carboxylic acid derivatives. In the case of an oxo group conjugated with a double bond, the formation of the ketal, enol ether or enol ester can be accompanied by a shift of the double bonds, for example in the case of the 3-oxo-$\Delta^4$ grouping, the 4,5-double bond shifts into the 5,6-position.

In resulting process products, free hydroxyl groups, especially secondary hydroxyl groups, can also be oxidised to oxo groups in a manner which is in itself known. Preferred oxidising agents are compounds of 6-valent chromium, such as chromium trioxide and chromic acid and its alkali metal salts, and lower alkanecarboxylic acids, such as acetic acid or propionic acid, or pyridine or acetone, optionally diluted with a halogenated lower alkane, such as methylene chloride or chloroform, and/or in the presence of aqueous sulphuric acid, are advantageously used as the reaction medium. Another preferred alternative for oxidation of the hydroxyl groups is the Oppenauer oxidation, that is to say oxidation with a ketone, such as acetone or cyclohexanone, under the catalytic influence of an aluminum lower alkoxide, such as aluminium isopropylate; this oxidation is advantageously employed for hydroxyl groups in the 17-position and especially in the 3-position and in the latter case especially because a double bond which may be present in the 5,6-position then shifts spontaneously into the 4,5-position. The Oppenauer oxidation is also successful in the case of esterified hydroxyl groups which are derived from acids which can be split off easily, for example from formic acid.

In resulting process products, oxo groups, especially the 3-oxo group and above all the 17-oxo group, can also be reduced to hydroxyl groups. The reduction is carried out in a manner which is in itself known and advantageously complex hydrides, especially those of aluminium or boron with an alkali metal or alkaline earth metal, such as, for example, sodium aluminium hydride, calcium borohydride, lithium borohydride but especially lithium aluminium hydride and above all sodium borohydride, or their derivatives in which one or more hydrogen atoms are replaced by lower alkoxy radicals, such as methoxy sodium borohydride and especially tri-tert.-butoxy lithium aluminium hydride, are used for this purpose. The choice of the solvent and of the reaction conditions depends on the reducing agent used and is in accord with the generally known principles. In the case of a selective reduction, for example that of the 17-oxo group, the other oxo groups are temporarily protected as ketals or enol esters or enol ethers and when a 3-oxo-$\Delta^4$ grouping is present, the procedure can also be that this is also reduced and thereafter selectively dehydrogenated, for example with manganese dioxide, back into the 3-oxo-$\Delta^4$ grouping.

However, the reduction of the oxo groups, above all the 17-oxo group, can also be carried out in a manner which is in itself known with simultaneous introduction of a hydrocarbon radical by reacting a corresponding oxo compound with an appropriate organometallic compound. When the hydrocarbon radical to be introduced in a lower alkyl radical, a Grignard compound, for example a lower alkyl-magnesium halide, such as methyl-magnesium bromide or methyl-magnesium iodide, or lower alkyl-lithium, such as methyl-lithium, is preferred as the organometallic compound; if a 1-alkynyl radical, especially the ethinyl radical, is to be introduced, a corresponding alkali metal compound, for example sodium acetylide or potassium acetylide or, in particular, lithium acetylide, is advantageously used. In the latter case it is particularly advantageous to use lithium acetylide in the form of its complex with ethylenediamine.

During these reactions, the other oxo groups must be protected in an analogous manner to that described above for the selective reduction. When the oxo group to be reacted is combined with one or two successive double bonds to form a conjugated system, such as is the case, in particular, in the 3-oxo-4,6-diene grouping, the reaction with a Grignard compound, especially a methyl-magnesium halide, can then be conducted in a known manner, especially in the presence of a copper-I salt, in such a way that the hydrocarbon radical to be introduced is introduced not on the carbon atom carrying the oxo group but on the carbon atom located at the end of the conjugated system, which formally corresponds to a 1,4- or 1,6-addition. The oxo group is converted to the hydroxyl group, which is then, however, in an enol grouping and is rearranged during working up to an oxo group, with formal saturation of the double bond. The 7α-methyl-3-oxo-4-ene grouping then results, for example, from the conjugated system indicated above by way of example.

Double bonds can also be introduced into the resulting end products in a manner which is in itself known. For example $\Delta^4$-3-oxo compounds, optionally in the form of their 3-enol acylates or 3-enol ethers, can be reacted with quinones, such as chloranil or, in particular, 2,3-dichloro-5,6-dicyano-1,4-benzoquinone, the 6,7-double bond and/or the 1,2-double bond being formed, depending on the choice of the reaction conditions, which are in themselves known, or, in the case of a 19-nor compound, aromatisation of the A ring can take place with the formation of the 3-hydroxy-1,3,5(10)-triene grouping in the same step, by rearrangement of the 3-oxo-1,4-diene grouping first formed. 1,2-dehydrogenation of $\Delta^4$-3-ketones can also be achieved in a manner which is in itself known by treatment with selenium dioxide, or microbiologically, for example by means of the micro-organisms Corynebacterium simplex or Septomyxa affinis; 6,7-dehydrogenation is also achieved by reacting an enol ether of a $\Delta^4$-3-ketone with manganese dioxide. However, double bonds can also be introduced in a known manner by splitting off the halogen from a halogen compound in the form of hydrogen halide; for example a $\Delta^{4,6}$-3-ketone is obtained in this way from a 6-halogeno-$\Delta^4$-3-ketone. For this purpose, the reaction with lithium carbonate or calcium carbonate, optionally in the presence of a lithium halide, such as lithium chloride or lithium bromide, in dimethylformamide or hexamethylphosphoric triamide, is particularly suitable.

The halogen compounds used for this purpose can be obtained in a manner which is in itself known by, for example, the addition of elementary halogen, such as chlorine or bromine, or a hypohalous acid, such as hypobromous acid or especially hypochlorous acid, to a double bond or to a system of two or more conjugated double bonds. For example, the procedure in the case of the introduction of a halogen atom, such as a chlorine or bromine atom, into the 6-position is advantageously such that elementary halogen, such as chlorine or bromine, or especially one of the abovementioned hypohalous acids, is allowed to act on a 3-enol ether or 3-enol ester, especially a 3-lower alkoxy-3,5-diene or a 3-lower alkanoyloxy-3,5-diene; the 3-oxo group is liberated during the reaction or at the latest during working up of the reaction mixture, so that a 6β-halogeno-$\Delta^4$-3-ketone results.

Amongst the 13-ethinyl-steroids obtainable according to the process, compounds of the general formula (Ia)

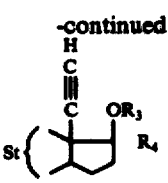

wherein St has the abovementioned meaning, $R_3$ denotes a hydrogen atom or a lower alkyl or lower alkanoyl group and $R_4$ denotes a hydrogen atom or a lower aliphatic hydrocarbon radical, especially a lower alkyl radical, above all the methyl or ethyl radical, or the ethinyl radical, are of particular interest.

Amongst the last-mentioned compounds of the formula Ia, those to be singled out because of their advantageous biological properties are those in which St represents a radical of the partial formula $St_1$ ($St_1$)

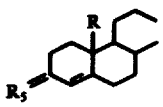

wherein $R_5$ denotes the oxo group, a hydrogen atom together with an esterified, or especially a free, hydroxyl group, or two hydrogen atoms and R denotes a hydrogen atom or the methyl group, it also being possible for an additional 1,2-double bond to be present in compounds in which R is the methyl group. These compounds are distinguished as highly active sex hormones. On the one hand, they have a central action in that they block the secretion of pituitary gonadotrophins; on the other hand they also have a peripheral action on the male and female sexual functions, as can be demonstrated by animal experiments. Because of these advantageous biological properties, they can be used in human medicine and veterinary medicine for all indications for which sex hormones are considered, but especially as preparations for inhibiting gonadotrophin secretion and/or for controlling fertility. 13-Ethinyl-17β-hydroxy-10-methyl-gon-4-en-3-one, which displays a marked androgenic activity in a dose of 0.01 mg/animal (capon, comb test, local application), as well as 13,17α-diethinyl-17β-hydroxy-gon-4-en-3-one, which exhibits a distinct gestagenic activity in a dosage range of 0.1 to 0.3 mg/kg and 0.3 mg/kg (rabbits, Clauberg test, subcutaneously and perorally respectively) and inhibits ovulation in a dosage range of 0.1 to 0.3 mg/kg (rats, ovulation test, perorally) are to be particularly singled out.

Because of their advantageous biological properties, those of the compounds characterised above, of the formula Ia, in which St represents a radical of the partial formula $St_2$ ($St_2$)

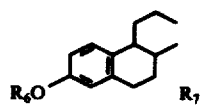

wherein $R_6$ denotes a hydrogen atom or a lower alkyl group, especially the methyl group, and $R_7$ denotes a hydrogen atom or the methyl group, are also to be mentioned. These compounds are distinguished both by a high oestrogenic activity and by substantial inhibition of the secretion of pituitary gonadotrophins. Because of these advantageous biological properties, they can be used as therapeutic preparations in human medicine and veterinary medicine for all indications for which oestrogens are customary, but especially in order to inhibit the gonadotrophin secretion and/or for controlling fertility. 13,17α-Diethinyl-3-methoxy-gona-1,3,5(10)-trien-17-ol, which has proved to have an oestrogenic action in the Allen-Doisy test in a dosage range of 0.3 to 1.0 mg/kg (perorally) and in the Fullbring-Burn test in a dosage range of 0.01 to 0.03 mg/kg (perorally), is to be singled out in particular.

The compounds of the general formula Ia, in which St corresponds to the radical $St_a$ characterised initially, are obtainable direct by means of the process according to the invention, which was described initially, without subsequent conversion. For example, the compounds of the formula Ia wherein St possesses the meanings of $St_2$ can be obtained in this way.

However, the last-mentioned compounds can also be manufactured in a manner which is in itself known, for example as described above, by aromatising the corresponding compounds of the formula Ia, in which St represents a radical of the partial formula $St'_2$ ($St'_2$)

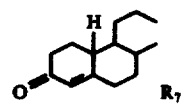

wherein $R_7$ has the abovementioned meaning, and, if desired, etherifying the product at the 3-hydroxyl group by means of a lower alkyl radical.

Those compounds of the formula Ia which contain a free 3-oxo group in the radical St, that is to say the compounds of the partial formula $St'_2$ or of the partial formula $St_1$, wherein $R_5$ denotes an oxo group, are not directly accessible by means of the process according to the invention on its own; in this case the 3-oxo group must be temporarily protected in a manner which is in itself known, for example as described above in the case of ketalisation and the formation of an enol ether, and the protective group must be removed again after the main reaction.

Alternatively, the procedure employed can also be such that the corresponding intermediate products of the formula Ia, wherein St represents a radical of the partial formula $St_3$ ($St_3$)

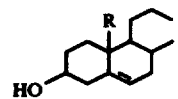

wherein R has the abovementioned meaning, are used as the starting materials. Appropriately, the 3-hydroxyl group in these intermediate products is oxidised in a known manner, for example as described above and in particular by means of the Oppenauer oxidation, to the 3-oxo group, with a simultaneous shift of the double bond into the 4,5-position. If desired, the 3-oxo group in resulting compounds can be reduced to a 3-hydroxyl group in the manner described above, and this can optionally be esterified or, when R represents the methyl group, a 1,2-double bond can be introduced in the manner already described.

Alternatively, the compounds of the formula Ia, characterised above, wherein St represents $St_1$, $St_2$, $St'_2$ or $St_3$, can also be manufactured by reducing the 17-oxo group in a corresponding 17-ketone of the general formula III

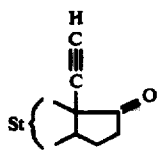
(III)

wherein St has the meanings indicated for $St_1$, $St_2$, $St'_2$ and $St_3$, to the hydroxyl group in the manner described above, the 3-oxo group being temporarily selectively protected if appropriate and a lower aliphatic hydrocarbon radical being introduced into the 17α-position if necessary, and, if desired, esterifying or etherifying the hydroxyl groups which are present, in the manner described above, and/or converting the radicals $St_1$-$St_3$ into one another in the manner described above.

The compounds of the general formulae Ia and III are also obtained when corresponding compounds in which one or more oxo groups are present in the form of a ketal, an enol ether or an enol acylate and/or one or more hydroxyl groups are present in the form of an ether, especially a silyl ether, are hydrolysed in a manner which is in itself known, especially as described above.

The invention also relates to the corresponding 13-(2-halogenovinyl)-steroids of the general formula

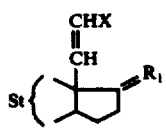
(IV)

wherein St and $R_1$ possess the abovementioned meanings and X represents bromine or chlorine and in which the hydrogen atoms of the halogenovinyl group are in the cis-position or the trans-position relative to the double bond, which arise as intermediate products. In general, the use of these compounds is analogous to that of the corresponding end products according to the invention. Preferred compounds of the general formula IV are those which are substituted in the manner as those preferred in the 13-ethinyl series, especially compounds of the general formula

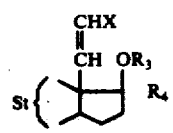
(IVa)

wherein X represents bromine and, above all, chlorine, and the hydrogen atoms of the halogenovinyl group are in the cis-position or trans-position relative to the double bond, St possesses the abovementioned meanings of $St_1$, $St_2$, $St'_2$ and $St_3$ and $R_3$ and $R_4$ have the abovementioned meanings.

Depending on the choice of the procedure and of the starting materials, the new compounds according to the invention can be present as mixtures of isomers or racemates. This arises in particular in the case of compounds which have been manufactured by total synthesis. Mixtures of isomers of this type, which may be obtained, can be separated into their individual components, on the basis of the physico-chemical differences between the components, in a known manner, for example by chromatography and/or fractional crystallisation. Racemates which may be obtained are first combined, in a manner which is in itself known, with an optically active compound, for example esterified with an optically active acid, and the mixture of isomers thus obtained is separated as indicated above. The individual antipodes are liberated from the individual components, thus obtained, in a manner which is in itself known, for example by hydrolysis.

The invention also relates to those embodiments of the above process in which a compound obtainable as an intermediate product at any stage is used as the starting material and the missing steps are carried out, or in which a starting material is formed under the reaction conditions.

The starting materials for the processes of the present invention are known or can be manufactured in a manner which is in itself known. Appropriately, the starting materials used are those which contain the substituents mentioned in particular above, and especially those which lead to the end products which have been described in particular or have been singled out by formulae.

The present invention also relates to the manufacture of pharmaceutical preparations for use in human medicine or veterinary medicine and of contraceptives for humans and mammals, which preparations and contraceptives contain, as active substances, the new pharmacologically active substances, described above, of the present invention, together with a pharmaceutical excipient. Excipients used are organic or inorganic substances which are suitable for enteral, for example oral, or parenteral administration or topical application. Substances which can be used to form the excipients are those which do not react with the new compounds, such as, for example, water, gelatine, lactose, starch, magnesium stearate, talc, vegetable oils, benzyl alcohols, gum, polyalkylene glycols, white petroleum jelly, cholesterol and other known excipients for medicaments. The pharmaceutical preparations can be in a solid form, for example as tablets, dragees or capsules, or in a liquid or semi-liquid form, as solutions, suspensions, emulsions, ointments or creams. If appropriate, these pharmaceutical preparations are sterilised and/or contain auxiliaries, such as preservatives, stabilisers, wetting agents or emulsifiers, salts for modifying the osmotic pressure or buffers. They can also contain further therapeutically valuable or biologically active substances.

The invention is described in more detail in the following examples, without being limited to what is disclosed therein.

EXAMPLE 1

A. 8.4 ml of a 1.56 molar solution of butyl-lithium in hexane is added to a suspension of 5.82 g of chloromethyltriphenyl-phosphonium chloride in 107 ml of absolute tetrahydrofurane and 1.67 ml of piperidine at 0° C, under argon and with complete exclusion of moisture. After 30 minutes, 1.3 g of 3,3:17,17-bis-(ethylenedioxy)- androst-5-en-18-al in 22.5 ml of tetrahydrofurane are added dropwise at room temperature. Thereafter, the mixture is stirred for 1 hour at room temperature and then poured into ice water. Ethyl acetate is added to the mixture and the organic phase is separated off and washed with cold 1 N hydrochloric acid, with water, with sodium bicarbonate solution and with saturated sodium chloride solution. After drying over sodium sulphate and evaporating the solvent, the residue is chromatographed on silica gel using a mixture of hexane/ethyl acetate (9:1). 3,3;17,17-Bis-(ethylenedioxy)-13-(cis-2-chlorovinyl)-10-methyl-gon-5-ene is isolated from the first fractions and is recrystallised from methylene chloride/hexane; melting point 172°–174° C, $[\alpha]_D 25 = -81°$. The corresponding trans isomer is obtained from the later fractions and after recrystallisation from petroleum ether melts at 108°–110° C, and has an $[\alpha]_D{}^{25} = -52°$.

B. 42 ml of a 1.5 molar solution of butyl-lithium in hexane are added to a solution of 850 mg of 3,3;17,17-bis-(ethylenedioxy)-13-(2-chlorovinyl)-10-methyl-gon-5-ene (a mixture of the cis and trans isomers in a ratio of 1:2) in 85 ml of absolute benzene in an argon atmosphere, whilst stirring, in the course of 6 hours at 70° C. After cooling, the reaction mixture is poured onto ice and taken up in ether. The organic phase, which is separated off, is washed with saturated sodium chloride solution until neutral, dried and evaporated in vacuo and the oily residue is chromatographed on silica gel. Elution with a mixture of hexane/ethyl acetate (4:1) gives pure 13-ethinyl-3,3;17,17-bis-(ethylenedioxy)-10-methyl-gon-5-ene, which after recrystallisation from ether/hexane melts at 159°–162° C.

C. 20 mg of p-toluenesulphonic acid are added to a solution of 327 mg of 13-ethinyl-3,3;17,17-bis-(ethylenedioxy)-10-methyl-gon-5-ene in 15 ml of acetone and 0.5 ml of water and the mixture is heated under reflux for 5 hours. The reaction mixture is concentrated to about 5 ml, diluted with ethyl acetate, washed with water and saturated sodium chloride solution, dried and evaporated. Chromatography on silica gel using a mixture of hexane/ethyl acetate (3:1) as the eluant gives only 13-ethinyl-10-methyl-gon-4-ene-3,17-dione, which is recrystallised from ether/hexane; melting point 148°–150° C, $[\alpha]_D{}^{25} = +63°$.

EXAMPLE 2

A. A solution of 2.92 g of 3β,17β-diacetoxy-androst-5-en-18-al in 30 ml of tetrahydrofurane is added dropwise to a solution of a Wittig reagent prepared from 7.83 g of chloromethyl-triphenyl-phosphonium chloride, 144 ml of tetrahydrofurane, 2.23 ml of piperidine and 11.25 ml of a 1.56 molar solution of butyl-lithium in hexane and the mixture is allowed to react for 40 minutes at room temperature and is worked up as indicated in Example 1. On purification by chromatography, as also indicated in Example 1A, this gives the cis and trans isomers of 3β,17β-diacetoxy-13-(2-chlorovinyl)-10-methyl-gon-5-ene in a ratio of 1:3. The cis isomer crystallises from methylene chloride/hexane and then melts at 161°–162° C; $[\alpha]_D{}^{25} = -70°$ (in chloroform); the trans isomer crystallises from methylene chloride/hexane, melting point 155°–156° C, $[\alpha]_D{}^{25} = -42°$ (in chloroform).

B. After adding 66 ml of a 10% strength aqueous potassium hydroxide solution, a solution of 1.68 g of 3β,17β-diacetoxy-13-(2-chlorovinyl)-10-methyl-gon-5-ene (a mixture of the cis and trans isomers in a ratio of 1:3) in 132 ml of methanol is stirred for 90 minutes at 45° C whilst passing nitrogen through the mixture. The reaction mixture is then concentrated to about 40 ml in a water pump vacuum and taken up in ethyl acetate. The organic phase, which is separated off, is washed with 1 N hydrochloric acid and with water until neutral, dried and evaporated. Chromatography on silica gel using a mixture of hexane/ethyl acetate (2:1) as the eluant gives 13-(2-chlorovinyl)-10-methyl-gon-5-ene-3β,17β-diol (a corresponding mixture of the cis and trans isomers) in an amorphous form.

C. A solution of 1.5 g of this mixture of isomers in 50 ml of dimethylformamide is mixed with 1.57 g of imidazole, the mixture is warmed to 35° C, 1.67 g of dimethyl-tert.-butyl-silyl chloride are added and the mixture is stirred for 16 hours at the said temperature. The reaction mixture is poured onto ice, taken up in ethyl acetate, washed with saturated sodium chloride solution, dried and evaporated. The residue is purified on silica gel using a mixture of hexane/ethyl acetate (99:1). This gives 13-(2-chlorovinyl)-3β,17β-bis-(dimethyl-tert.-butylsilyloxy)-10-methyl-gon-5-ene (a mixture of the cis and trans isomers); IR spectrum: 3,300, 2,900, 2,150, 1,095, 880 and 812 cm$^{-1}$.

D. A solution of 1.8 g of the mixture of isomers, thus obtained, in 180 ml of absolute benzene is warmed to 40° C and 45 ml of a 1.5 molar solution of butyl-lithium in hexane is added at this temperature in the course of 16 hours. After cooling, the reaction mixture is poured onto ice, taken up in ether, washed with saturated sodium chloride solution, dried and evaporated. The resulting crude 13-ethinyl-3β,17β-bis-(dimethyl-tert.-butylsilyloxy)-10-methyl-gon-5-ene is further processed without additional purification.

E. The crude bis-silyl ether obtained according to the preceding Example 2D is stirred in 94 ml of acetonitrile and 11 ml of 1 N hydrochloric acid for 18 hours at room temperature. The reaction mixture is concentrated in vacuo to about 20 ml and extracted with ethyl acetate. The organic phase is washed with water and saturated sodium chloride solution, dried and evaporated, by which means 13-ethinyl-10-methyl-gon-5-ene-3β,17β-diol is obtained; IR spectrum: 3,580, 3,295, 2,940, 2,100, 1,040 and 1,025 cm$^{-1}$.

EXAMPLE 3

A solution of 900 mg of the crude 13-ethinyl-10-methyl-gon-5-ene-3β,17β-diol, obtained according to Example 2E, and 540 mg of aluminium isopropylate in 135 ml of toluene and 5.4 ml of cyclohexanone is boiled under reflux, under a water separator, for 60 minutes. After cooling, the reaction mixture is diluted with ethyl acetate, washed with potassium sodium tartrate solution, water and saturated sodium chloride solution, dried and evaporated. The oily residue is chromatographed on 80 g of silica gel. Using a mixture of hexane/ethyl acetate (3:1), 13-ethinyl-10-methyl-gon-4-ene-3,17-dione is eluted, melting point 148°–150° C; $[\alpha]_D{}^{25} = +63°$, after which 13-ethinyl-17β-hydroxy-10-methyl-gon-4-en-3-one, melting point 147°–149° C, $[\alpha]_D{}^{25} = +154°$, is obtained by elution with a mixture of the same solvents in a ratio of 2:1.

EXAMPLE 4

A small excess of Jones reagent (8 N chromic acid in sulphuric acid) is added to a solution of 300 mg of 13-ethinyl-17β-hyroxy-10-methyl-gon-4-en-3-one in 4 ml of acetone at 0° C. The reaction mixture is stirred for a further 5 minutes at 0° C and the excess reagent is destroyed by adding isopropyl alcohol. The reaction mixture is diluted with ethyl acetate, washed with water, sodium bicarbonate solution and saturated sodium chloride solution, dried and evaporated. The residue is chromatographed on silica gel; elution with a mixture of hexne/ethyl acetate (3:1) gives 13-ethinyl-10-methyl-gon-4-ene-3,17-dione, which is identical to the product of Examples 1C and 3.

EXAMPLE 5

A mixture of 1.2 g of 13-ethinyl-10-methyl-gon-4-ene-3,17-dione, 20 ml of dioxane, 2 ml of orthoformic acid ethyl ester and 60 mg of p-toluenesulphonic acid is stirred at room temperature for 3¾ hours with exclusion of light. The reaction mixture is poured into 150 ml of water containing 5 drops of pyridine and extracted twice with ethyl acetate and the organic layer is washed with water and saturated sodium chloride solution until neutral, dried and evaporated in a water pump vacuum. The crystalline crude 13-ethinyl-3-ethoxy-10-methyl-gona-3,5-dien-17-one, which is obtained, is then dissolved in 20 ml of dioxane and the solution is added dropwise, in the course of 30 minutes, to a solution, which is saturated with acetylene, of 6 g of a lithium acetylide/ethylenediamine complex in 60 ml of dioxane, whilst passing acetylene through the mixture at the same time. The reaction mixtue is then stirred for a further 15 minutes at room temperature and treated, whilst cooling, with saturated ammonium chloride solution and with ethyl acetate and the organic phase is washed successively with 1 N hydrochloric acid and saturated sodium chloride solution, dried and evaporated in a water pump vacuum.

The resulting oily residue of the corresponding 13,17α-diethinyl-enol ether is dissolved in 10 ml of tetrahydrofurane, 5 ml of a mixture of concentrated hydrochloric acid and water in a ratio of 3:7 are added and the mixture is stirred for 1 hour. After adding ethyl acetate, the organic layer is washed with sodium bicarbonate solution and water until neutral, dried and evaporated in a water pump vacuum. The residue is chromatographed on the 100-fold amount of silica gel using a mixture of hexane/ethyl acetate (3:1) as the eluant. This gives 13,17α-diethinyl-17-hydroxy-10-methyl-gon-4-en-3-one; melting point 155°–156° C; $[\alpha]_D^{25} = +47°$ (in chloroform).

EXAMPLE 6

A. A solution of a Wittig reagent is prepared from 14.6 g of chloromethyl-triphenyl-phosphonium chloride, 260 ml of tetrahydrofurane, 16 ml of piperidine and 30 ml of a 1.56 molar solution of butyl-lithium in hexane and a solution of 3.2 g of 3,17-dioxo-oestr-4-en-18-al 3,17-bis-ethylene ketal in 50 ml of tetrahydrofurane is added dropwise and the mixture is allowed to react for 60 minutes at room temperature. After working up according to the instructions of the preceding examples and chromatography on silica gel using a mixture of hexane/ethyl acetate (2:1) as the eluant, a mixture of the cis and trans isomers of 13-(2-chlorovinyl)-gon-4-ene-3,17-dione 3,17-bis-ethylene ketal is obtained as a colourless foam.

B. 20 ml of a 1.56 molar solution of butyl-lithium in hexane are added dropwise, in the course of 3 hours, to a solution of 2 g of 13-(2-(chlorovinyl)-gon-4-ene-3,17-dione 3,17-bis-ethylene ketal (the mixture of the cis and trans isomers obtained above) in 200 ml of absolute benzene at 70° C, under argon and whilst stirring. The reaction mixture is then cooled to 5° C, poured into ice water and extracted with ethyl acetate. The organic phase is washed with 1 N hydrochloric acid, with saturated sodium chloride solution and with saturated sodium bicarbonate solution, dried over sodium sulphate and evaporated in vacuo. The residual crude product consists mainly of 13-ethinyl-gon-4-ene-3,17-dione 3,17-bis-ethylene ketal (a mixture of the $\Delta^5$ and $\Delta^{5(10)}$ isomers ) and is used without purification for the subsequent hydrolysis.

C. The crude product from the preceding state is warmed in 28 ml of glacial acetic acid and 14 ml of water, first to 60° C for 2 hours and then to 85° C for 2 hours. The reaction mixture is then concentrated to about 10 ml in a water pump vacuum, taken up in ethyl acetate, washed three times with sodium chloride solution, dried and evaporated. Chromatography of the residue on silica gel, using a mixture of hexane/ethyl acetate (3:1) as the eluant, gives pure 13-ethinyl-gon-4-ene-3,17-dione, which when recrystallised from methylene chloride/acetone/hexane melts at 167°–169° C.

EXAMPLE 7

A mixture of 600 mg of 13-ethinyl-gon-4-ene-3,17-dione, 10 ml of dioxane, 1 ml of orthoformic acid ethyl ester and 30 mg of p-toluenesulphonic acid is left to stand in the dark for 4 hours at room temperature. The reaction mixture is then discharged into ice water (containing traces of pyridine) and extracted twice with ethyl acetate and the extracts are washed until neutral, dried and evaporated. The crude crystalline 13-ethinyl-3-ethoxy-gona-3,5-dien-17-one is then dissolved in 16 ml of dioxane and the solution is added dropwise, in the course of 30 minutes, to a solution, saturated with acetylene, of 4 g of a lithium acetylide/ethylenediamine complex in 40 ml of dioxane, whilst passing acetylene through the mixture at the same time. Thereafter, the reaction mixture is stirred at room temperature for 30 minutes, then treated, whilst cooling, with saturated ammonium chloride solution and with ethyl acetate and the organic phase is washed successively with 1 N hydrochloric acid and a saturated sodium chloride solution, dried and evaporated in vacuo. The resulting oily residue of the crude 13,17α-diethinyl-3-ethoxy-gona-3,5-dien-17-ol is stirred in 15 ml of tetrahydrofurane and 8 ml of a 3:7 mixture of concentrated hydrochloric acid and water for 30 minutes at room temperature. After adding ethyl acetate, the organic layer is washed with sodium bicarbonate solution and water until neutral, dried and evaporated in a water pump vacuum. The residue is chromatographed on silica gel using a mixture of hexane/ethyl acetate (3:1) as the eluant; this gives 13,17α-diethinyl-17-hydroxy-gon-4-en-3-one, which after recrystallisation from methylene chloride/ether/hexane melts at 206°–208° C.

EXAMPLE 8

A. A solution of a Wittig reagent is prepared from 12.9 g of chloromethyl-triphenyl-phosphonium chloride, 150 ml of tetrahydrofurane, 3,6 ml of piperidine and 24.6 ml of a 1.56 molar solution of butyl-lithium in hexane and a solution of 4.2 g of 17β-acetoxy-3 -methoxy-oestra-1,3,5(10)-trien-18-al in 50 ml of tetrahydrofurane is added dropwise and the mixture is left to react for 10 minutes at room temperature. After working up according to the instructions of the preceding examples and chromatography on silica gel using a mixture of hexane/ethyl acetate (9:1) as the eluant, a mixture of the cis and trans isomers of 17β-acetoxy-13-(chlorovinyl)-3-methoxy-gona-1,3,5(10)-triene is obtained.

B. After adding 160 ml of a 2.5% strength potassium hydroxide solution, a solution of 4.0 g of 17β-acetoxy-13-(2-chlorovinyl)-3-methoxy-gona-1,3,5(10)-triene (a mixture of the cis and trans isomers) in 320 ml of methanol is stirred for 90 minutes at 45° C, whilst passing nitrogen through the mixture. The reaction mixture is then concentrated to about 50 ml in a water pump vacuum, taken up in methylene chloride, washed with 1 N hydrochloric acid and water, dried and evaporated. The residue is purified on silica gel, using a mixture of hexane/ethyl acetate (3:1) as the eluant, by which means amorphous 13-(2-chlorovinyl)-3-methoxy-gona-1,3,5(10)-trien-17β-ol (mixture of the cis and trans isomers) is obtained.

C. A solution of 3.0 g of this mixture of isomers in 100 ml of dimethylformamide is mixed with 1.55 g of imidazole, the mixture is warmed to 35° C and 1.63 g of dimethyl-tert.-butyl-silyl chloride are added. The mixture is left to stir for 18 hours at this temperature and is then poured onto ice, taken up in ethyl acetate, washed with saturated sodium chloride solution, dried and evaporated. The residue is purified on silica gel, using a mixture of hexane/ethyl acetate (95:5), by which means 13-(2-chlorovinyl)-17β-dimethyl-tert.-butyl-silyloxy-3-methoxy-gona-1,3,5(10)-triene is obtained as a mixture of the cis and trans isomers.

D. A solution of 3.5 g of the resulting mixture of the cis and trans isomers in 350 ml of absolute benzene is warmed to 40° C and 80 ml of a 1.5 molar solution of butl-lithium in hexane are added in the course of 3 hours. After cooling, the reaction mixture is poured onto ice, taken up in ethyl acetate, washed twice with saturated sodium chloride solution, dried and evaporated. The residue consists in the main of 13-ethinyl-17β-dimethyl-tert.-butylsilyloxy-3-methoxy-gona-1,3,5(10)-triene and is used direct, without additional purification, for splitting the silyloxy group.

E. 20 ml of 1 N hydrochloric acid are added to a solution of the crude 13-ethinyl-17β-dimethyl-tert.-butylsilyloxy-3-methoxy-gona-1,3,5(10)-trien, obtained according to the preceding paragraph, in 180 ml of acetonitrile and the mixture is left to stir for 2 hours at 40° C. The reaction mixture is poured onto sodium bicarbonate/ice water and taken up in ethyl acetate and the organic phase is washed with water and saturated sodium chloride solution, dried and evaporated. The residue is chromatographed on silica gel using a mixture of hexan/ethyl acetate (9:1) as the eluant. This gives pure 13-ethinyl-3-methoxy-gona-1,3,5(10)-trien-17β-ol, which after recrystallisation from methylene chloride/hexane has a melting point of 127°-128° C and an $[\alpha]_D^{25}$ of +89°.

EXAMPLE 9

A small excess of Jones reagent (mixture of 8 N chromic acid and sulphuric acid) is added to 1.8 g of 13-ethinyl-3-methoxy-gona-1,3,5(10)-trien-17β-ol in 40 ml of acetone at 0° C, the mixture is stirred for 5 minutes at 0° C, the excess of reagent is destroyed by adding isopropyl alcohol and the mixture is diluted with ethyl acetate, washed with water, sodium bicarbonate solution and saturated sodium chloride solution, dried and evaporated. The residue is chromatographed on silica gel using a mixture of hexane/ethyl acetate (9:1) as the eluant, by which means pure 13-ethinyl-3-methoxy-gona-1,3,5(10)-trien-17-one is obtained; melting point 177°-178° C; $[\alpha]_D^{25}$ = +86°.

EXAMPLE 10:

A solution of 1.2 g of 13-ethinyl-3-methoxy-gona-1,3,5(10)-trien-17-one in 20 ml of dioxane is added dropwise, in the course of 30 minutes, to a solution, saturated with acetylene, of 6 g of a lithium acetylide/ethylenediamine complex in 60 ml of dioxane, whilst at the same time passing acetylene through the mixture. The reaction mixture is stirred for a further 60 minutes at room temperature and, whilst cooling, is treated with saturated ammonium chloride solution and with ethyl acetate. The organic phase is washed successively with 1 N hydrochloric acid and a saturated sodium chloride solution, dried and evaporated in a water pump vacuum. The residue is chromatographed on silica gel using a mixture of hexane/ethyl acetate (9:1) as the eluant and this gives 13,17α-diethinyl-3-methoxy-gona-1,3,5(10)-trien-17β-ol, which after recrystallisation from acetone/hexane has a melting point = 177°179° C and a $[\alpha]_D^{25}$ = −11°.

We claim:

1. Process for the manufacture of 13-ethinyl-steroids of the general formula I

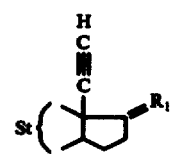

(I)

wherein St denotes the remaining part of a steroid compound, and $R_1$ denotes a member of the group consisting of a free oxo group, a ketalised oxo group, a free, etherified or esterified hydroxyl group together with a hydrogen atom, a free, etherified or esterified hydroxyl group together with a lower aliphatic hydrocarbon radical, and a free, etherified or esterified hydroxyl group together with a halogenated lower aliphatic hydrocarbon radical, characterised in that a corresponding 13-formyl-steroid of the general formula II

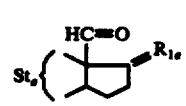

(II)

wherein $St_a$ denotes a radical which corresponds to the radical St characterised above and in which, apart from the 11-oxo group, there are no free oxo groups, and $R_{1a}$ denotes a radical which corresponds to the radical $R_1$ characterised above and in which no free oxo group is present, is subjected to a Wittig reaction with a bromomethylenephosphorane or chloromethylenephosphorane compound which carries three further hydrocarbon radicals on the phosphorus atom, and a resulting 13-(2-halogenovinyl) compound is dehydrohalogenated by means of an extremely strong base selected from the group consisting of potassium tert.-butylate in a polar solvent, an alkali metal amide in ammonia and an organometallic compound derived from an alkali metal.

2. Process according to claim 1, characterised in that the Wittig reaction is carried out with chloromethylenetriphenylphosphorane.

3. Process according to claim 1, characterised in that dehydrohalogenation is effected by means of butyl-lithium.

4. Process according to claim 1, characterised in that a steroid compound of the formula II wherein $R_{1a}$ denotes the ethylenedioxy group, or a β-oriented lower alkanoyloxy group together with a hydrogen atom, is used as the starting material.

5. Process according to claim 1, characterised in that an intermediate 13-(2-chlorovinyl)-steroid wherein any hydroxyl groups which may be present are in an etherified form is dehydrohalogenated.

6. Process according to claim 5, characterised in that a compound wherein the hydroxyl groups are present as silyl ethers is dehydrohalogenated.

7. 13-Ethinyl-steroids of the general formula

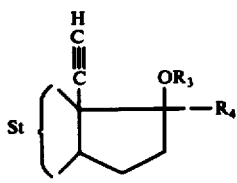

wherein $R_3$ denotes a hydrogen atom or a lower alkyl or lower alkanoyl group, $R_4$ denotes a hydrogen atom or a lower aliphatic hydrocarbon radical, or $OR_3$ and $R_4$ together denote an oxo group, and St represents a residue selected from a group consisting of residues of the partial formulae

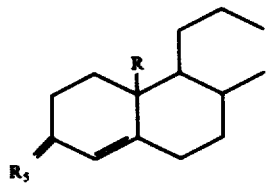

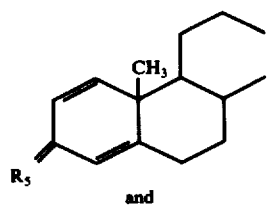

and

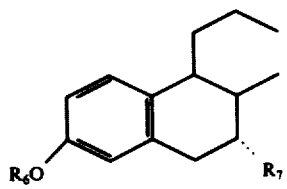

wherein R and $R_7$ each denotes a hydrogen atom or the methyl group, $R_5$ denotes an oxo group, a hydrogen atom together with a free hydroxyl group, a hydrogen atom together with an esterified hydroxyl group, or two hydrogen atoms, and $R_6$ denotes a hydrogen atom or a lower alkyl group.

8. A compound according to claim 7, of the general formula IA

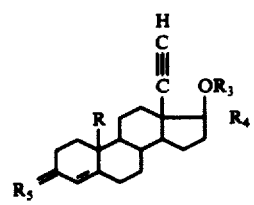

(IA)

wherein R denotes a hydrogen atom or the methyl group, $R_3$ denotes a hydrogen atom or a lower alkyl or lower alkanoyl group, $R_4$ denotes a hydrogen atom or a lower aliphatic hydrocarbon radical, or $OR_3$ and $R_4$ together denote an oxo group, and $R_5$ denotes the oxo group, a hydrogen atom together with an esterified or free hydroxyl group, or two hydrogen atoms, or a corresponding 1,2-dehydro analogue thereof in which R is the methyl group.

9. A compound according to claim 7, of the general formula (IB)

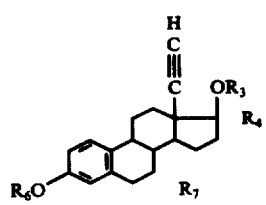

(IB)

wherein $R_3$ and $R_4$ have the meaning indicated in claim 8 and $R_6$ denotes a hydrogen atom or a lower alkyl group and $R_7$ denotes a hydrogen atom or the methyl group.

10. A compound of the general formula (IC)

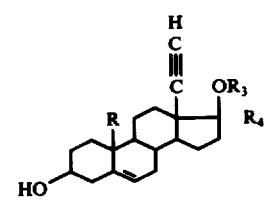

(IC)

wherein R, $R_3$ and $R_4$ have the meaning indicated in claim 8, or a 3-ester thereof.

11. A compound according to claim 7, selected from the group consisting of
13-ethinyl-17β-hydroxy-10-methyl-gon-4-en-3-one,
13,17α-diethinyl-17-hydroxy-10-methyl-gon-4-en-3-one,
13,17α-diethinyl-17-hydroxy-gon-4-en-3-one,
13-ethinyl-3-methoxy-gona-b 1,3,5(10)-trien-17β-ol,
13-ethinyl-3-methoxy-gona-1,3,5(10)-trien-17-one, and
13,17α-diethinyl-3-methoxy-gona-1,3,5(10)-trien-17-ol.

12. The compound 13,17α-diethinyl-17-hydroxy-gon-4-en-3-one according to claim 8.

13. The compounds 13,17α-diethinyl-3-methoxy-gona-1,3,5(10)-trien-17β-ol according to claim 9.

14. The compound 13-ethynyl-3-methoxy-gona-1,3,5(10)-trien-17β-ol according to claim 9.

* * * * *